United States Patent
Bruder et al.

(10) Patent No.: US 11,090,135 B2
(45) Date of Patent: Aug. 17, 2021

(54) SYNERGISTIC ULTRASONIC, SONIC OR ELECTRIC ENERGY AND LIGHT TRANSMITTING PROBE FOR DISINFECTION OF ROOT CANALS DURING AN ENDODONTIC PROCEDURE

(71) Applicant: SYACT LLP, Plantation, FL (US)

(72) Inventors: George Bruder, West Palm Beach, FL (US); Sergio Kuttler, Plantation, FL (US); Anil Kishen, Mississauga (CA)

(73) Assignee: SYACT, LLP, Plantation, FL (US)

( * ) Notice: Subject to any disclaimer, the term of this patent is extended or adjusted under 35 U.S.C. 154(b) by 30 days.

(21) Appl. No.: 16/091,627

(22) PCT Filed: Apr. 5, 2017

(86) PCT No.: PCT/US2017/026108
§ 371 (c)(1),
(2) Date: Oct. 5, 2018

(87) PCT Pub. No.: WO2017/176863
PCT Pub. Date: Oct. 12, 2017

(65) Prior Publication Data
US 2019/0159867 A1  May 30, 2019

Related U.S. Application Data

(60) Provisional application No. 62/318,551, filed on Apr. 5, 2016.

(51) Int. Cl.
*A61C 5/40* (2017.01)
*A61N 5/06* (2006.01)
(Continued)

(52) U.S. Cl.
CPC ........... *A61C 5/40* (2017.02); *A61B 1/04* (2013.01); *A61B 1/0607* (2013.01);
(Continued)

(58) Field of Classification Search
CPC .................. A61C 1/0046; A61C 5/40
See application file for complete search history.

(56) References Cited

U.S. PATENT DOCUMENTS 5,030,090 A * 7/1991 Maeda ............. A61C 1/0046
433/216
5,071,222 A  12/1991 Laakmann et al.
(Continued)

FOREIGN PATENT DOCUMENTS

WO  2003061514 A1  7/2003
WO  2016036579 A1  3/2016

OTHER PUBLICATIONS

Robert C. Miller "Optical Fiber" How Products are Made, Available as of on Mar. 28, 2016 per https://web.archive.org/web/20160328143322/http://www.madehow.com/Volume-1/Optical-Fiber.html>.
(Continued)

*Primary Examiner* — Ralph A Lewis
(74) *Attorney, Agent, or Firm* — Sandberg Phoenix & von Gontard, P.C.

(57) ABSTRACT

A light transmitting probe for use in endodontic procedures comprises a light transmitting core and a metallic sheath surrounding said core. The metallic sheath defines a reflective inner surface. The probe further includes a plurality of apertures formed in the sheath, such that light can exit said probe through the apertures.

21 Claims, 2 Drawing Sheets

(51) Int. Cl.
  *A61B 1/04* (2006.01)
  *A61B 1/06* (2006.01)
  *A61B 1/07* (2006.01)
  *A61B 1/24* (2006.01)
  *A61C 3/03* (2006.01)
  *A61B 18/00* (2006.01)
  *A61B 18/22* (2006.01)

(52) U.S. Cl.
  CPC .............. *A61B 1/0615* (2013.01); *A61B 1/07* (2013.01); *A61B 1/24* (2013.01); *A61C 3/03* (2013.01); *A61N 5/0624* (2013.01); *A61B 18/22* (2013.01); *A61B 2018/00994* (2013.01); *A61B 2018/2261* (2013.01); *A61N 5/062* (2013.01); *A61N 2005/063* (2013.01); *A61N 2005/0643* (2013.01)

(56) References Cited

U.S. PATENT DOCUMENTS

| | | | | |
|---|---|---|---|---|
| 5,092,773 A * | 3/1992 | Levy | ............... | A61C 1/0046 433/224 |
| 5,271,734 A | 12/1993 | Takeuchi | | |
| 5,503,559 A * | 4/1996 | Vari | ............... | A61B 5/0088 433/102 |
| 6,039,565 A * | 3/2000 | Chou | ............... | A61C 1/0046 433/119 |
| 6,418,252 B1 * | 7/2002 | Maitland | ............... | G02B 6/0008 385/31 |
| 7,040,892 B2 * | 5/2006 | Hirszowicz | ............... | A61C 1/0046 433/215 |
| 7,748,979 B2 * | 7/2010 | Nahlieli | ............... | A61B 1/247 433/29 |
| 8,221,117 B2 * | 7/2012 | Rizoiu | ............... | A61C 1/0046 433/224 |
| 2005/0171408 A1 | 8/2005 | Parker | | |
| 2009/0130622 A1 * | 5/2009 | Bollinger | ............... | A61C 1/0046 433/29 |
| 2009/0298004 A1 | 12/2009 | Rizoiu | | |
| 2011/0217665 A1 | 9/2011 | Walsh et al. | | |
| 2019/0159867 A1 * | 5/2019 | Bruder | ............... | A61H 23/0245 |

OTHER PUBLICATIONS

International Search Report for corresponding PCT/2017/026108 dated Jul. 6, 2017.
Written Opinion for corresponding PCT/2017/026108 dated Jul. 6, 2017.

* cited by examiner

SYNERGISTIC ULTRASONIC, SONIC OR ELECTRIC ENERGY AND LIGHT TRANSMITTING PROBE FOR DISINFECTION OF ROOT CANALS DURING AN ENDODONTIC PROCEDURE

CROSS-REFERENCE TO RELATED APPLICATIONS

This application is the US National Stage of Intl App. No. PCT/US2017/026108 under 35 USC 0.5371 which claims priority to U.S. App. No. 62/318,551 filed Apr. 5, 2016, the contents of both applications being incorporated herein by reference.

STATEMENT REGARDING FEDERALLY SPONSORED RESEARCH OR DEVELOPMENT

Not Applicable.

BACKGROUND OF THE INVENTION

This invention relates to a tip comprising a light guide or probe used to activate fluids in a root canal during the disinfection step of an endodontic treatment, and in particular, to such a light guide or probe, which also transmits light into the root canal.

Central to a successful endodontic (or root canal) treatment has been the use of chemical reagents during mechanical root canal shaping procedures to completely clean all aspects of the root canal system. The chemicals used to enhance canal debridement and disinfection during cleaning and shaping procedures potentially reach all aspects of the root canal system. The most common chemicals currently used during canal preparation to actively assist in cleaning and disinfecting include bleach i.e., sodium hypochlorite (NaOCl), hydrogen peroxide ($H_2O_2$), and chelating agents. Often, a 2%-6% solution of sodium hypochlorite (NaOCl) and ethylenediaminetetraacetic acid (EDTA, such as available under the brand name REDTA) or the salt of a weak chelator, such as 1 hydroxyethylidene-1, 1-bisphosphonate or etidronate (HEDP) is used.

During canal preparation, a solution of NaOCl is liberally irrigated into the root canal space where its solvent action facilitates the digestion and removal of pulp tissue (which contains blood vessels, connective tissue, and nerves), biofilm (which can include microbes, antigens, viruses, spores), endotoxins and other irritants generated by the microorganisms. This solution has the potential to circulate, penetrate and, hence, clean into all aspects of the root canal space. However, studies have shown that even the combined use of endodontic instruments and sodium hypochlorite (NaOCl) does not remove all the biofilm (including bacteria) and material from the root canal and pulp chamber. The walls of a root canal are comprised of dentin, which contains millions of dentinal tubules per square millimeter. Instruments used to negotiate and shape a canal cut organic and inorganic dentin, which, in combination with organic substrates, forms dentinal mud. Dentinal mud, pulp tissue, microbes, antigens, and other related irritants have been consistently visualized histologically after cleaning and shaping procedures in the dentinal tubules and various aspects of the root canal systems. Thus, after cleaning and shaping procedures, the root canal is still covered with a film of debris, frequently described in the literature as a "smear layer." This "smear layer" includes dentinal mud and/or organic and inorganic debris, including the irritants noted above.

After cleaning and shaping, the root canal has been traditionally filled with an obturation material (e.g., gutta percha) and a root sealer. However, if the smear layer or film is not adequately removed from the root canal, the smear layer can compromise the filling and sealing of the root canal system. If cleaning, shaping, or obturation is incomplete then the root canal space is predisposed to bacterial leakage and failure. Post-treatment failures attributable to leakage are common and require endodontic retreatment of the tooth or extraction. Thus, a systematic removal of tissue and complete and thorough removal of the smear layer or film should be completed. To address the smear layer, practitioners use a combination of a weak acid, such as 17% EDTA, and surfactants in an effort to remove the smear layer. Typically, the root canal is flushed with an aqueous solution of EDTA, or other final rinse solutions, to accomplish this. Traditionally, practitioners have used a combination of hand and rotary root canal file(s) or a cannula to activate the solution and enhance the performance of the EDTA. These devices may be used manually or mounted in a manual, sonic or ultrasonic handpiece to produce vibrations and fluid movement. As an example, even when a file is used, it is impossible to ensure that the file is brought into contact with the complete surface of the root canal, and hence it is difficult to ensure that substantially all of the smear layer has been removed. Regrettably, the use of ultrasonically driven metal instruments has frequently led to iatrogenic events, such as broken instruments, ledges in the wall of the root canal preparation, or even perforation of the root canal. Hence the use of such instruments is not desirable.

WO2016036579 discloses a photo-chemically activated micro-bubble based root canal disinfection method. This method requires the introduction of light into the root canal to activate a photoactive solution. As is known, light in the visible wavelengths (i.e., visible light) is used to activate photoactive solutions. However, we know of no tip or probe which can introduce light into the root canal and which can simultaneously activate the solution with other forms of energy such as manual, ultrasonic or sonic or electrical energy.

SUMMARY

Briefly stated, a tip for use in endodontic procedures comprises a probe having a light transmitting core and a metallic sheath surrounding the core. The sheath defines a reflective inner surface, and the probe includes a plurality of apertures formed in the sheath, such that light can exit the probe through the apertures.

In one aspect of the probe, the probe defines a light zone and a connecting portion, and the apertures are preferably all formed in the light zone. In this light zone, light can exit the probe, and optionally, reflected light can enter the probe to facilitate visualization of the root canal.

In another aspect of the probe, the apertures are defined by a plurality of perforations and/or slits in the sheath.

In another aspect of the probe, the apertures are shaped and configured such that a greater amount of light can exit the side of probe in a bottom portion of the light zone than in an upper portion of the light zone. Accordingly, the probe can be formed (a) with the apertures being of substantially constant size with more apertures in the bottom portion of the light zone than in the upper portion of the light zone; and/or (b) with the apertures in the bottom portion of the light zone being greater in size than the apertures in the upper portion of the light zone.

In accordance with an aspect of the probe, the core is comprised of a single light transmitting optical fiber or a plurality of light transmitting optical fibers. If the core is formed of a plurality of optical fibers, the optical fibers can be of differing lengths.

In accordance with an aspect of the probe, the probe includes a camera, and at least one of the optical fibers directs light coronally from within the root canal to be received by the camera. As can be appreciated, light reflected from the root canal enters the probe in the light zone to be received by the camera. The camera is in communication with a receiver which is adapted to display the image of the root canal received by the camera.

In accordance with an aspect of the probe, the metallic sheath is electrically conductive; and the probe is adapted to connect the sheath to a source of electricity, such that the probe can induce an electrical field in the root canal.

In accordance with an aspect of the probe, the probe is adapted to be connected to a sonic or ultrasonic drive, such that the probe will vibrate sonically or ultrasonically when the drive is activated. Alternatively, the probe can be provided with a handle to be manually activated, that is, a practitioner can rotate the probe or move the probe vertically within the canal by hand.

In accordance with an aspect of the probe, the sheath is formed by coating the light transmitting core with a desired metal, such as by thin film deposition, sputter coating technology, or electrophoretic deposition. Alternatively, the probe can be formed by co-extruding the core and the sheath or by 3D printing.

In accordance with an aspect of the probe, the sheath is made from a metal oxide, gold, palladium, chromium, silver, and combinations thereof.

In accordance with an aspect of the probe, the probe can be generally straight, generally C-shaped, or generally S-shaped. Further, regardless of the shape, the probe can be generally planar or 3-dimensional (i.e., be formed in more than one plane).

In accordance with another aspect, the probe can be generally circular or oval in cross-section. Additionally, whether circular or oval, the probe can be provided with one, two, three, four or more grooves extending longitudinally along an outer surface of said probe. If there are two or more grooves, the grooves can be evenly or unevenly spaced about said probe. Further, the grooves can all be the same size or they can be of different sizes.

The probe can include only one of the above noted aspects or one or more of the above noted aspects in any combination.

BRIEF DESCRIPTION OF THE DRAWINGS

Corresponding reference numerals will be used throughout the several figures of the drawings.

DETAILED DESCRIPTION

Figure 1:
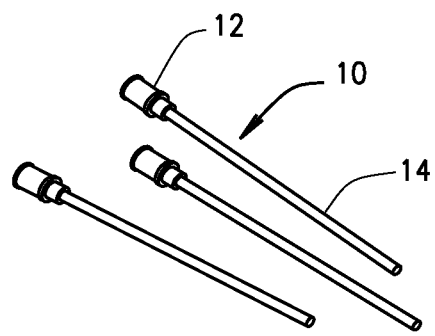
FIG. 1 is perspective view of a grouping of tips having light transmitting probes.

The following detailed description illustrates the claimed invention by way of example and not by way of limitation. This description will clearly enable one skilled in the art to make and use the claimed invention, and describes several embodiments, adaptations, variations, alternatives and uses of the claimed invention, including what I presently believe is the best mode of carrying out the claimed invention. Additionally, it is to be understood that the claimed invention is not limited in its application to the details of construction and the arrangements of components set forth in the following description or illustrated in the drawings. The claimed invention is capable of other embodiments and of being practiced or being carried out in various ways. Also, it is to be understood that the phraseology and terminology used herein is for the purpose of description and should not be regarded as limiting.

A tip 10 is shown generally in FIG. 1. The tip 10 comprises a connector 12 with probe 14 extending therefrom. As will become evident from the discussion below, the probe 14 is operable to deliver light apically into the canal and to transmit light coronally from within the canal. The probe can thus be considered to be a light guide. The connector 12 is configured to connect the tip 10 to a sonic or ultrasonic driver which will induce either sonic or ultrasonic vibrations in the tip upon activation of the driver. The driver can be, for example, a driver such as is available from Dentsply-Sirona under the name ENDOACTIVATOR® which utilizes a snap-type connection of the tip to the driver. The driver could be any other type of commercially available driver. The connector 12 can, for example, be a threaded connector, a Luer Lock connector, a plug-type connector, or any other type of connector which will secure the tip 10 to the driver, such that the driver will induce vibrations in the probe 14 upon activation of the tip. Alternatively, the tip 10 can include a handle which can be grasped by a practitioner to enable the practitioner to manually rotate the probe or move the probe vertically (i.e., up and down) in the root canal.

Figures 2, 3:
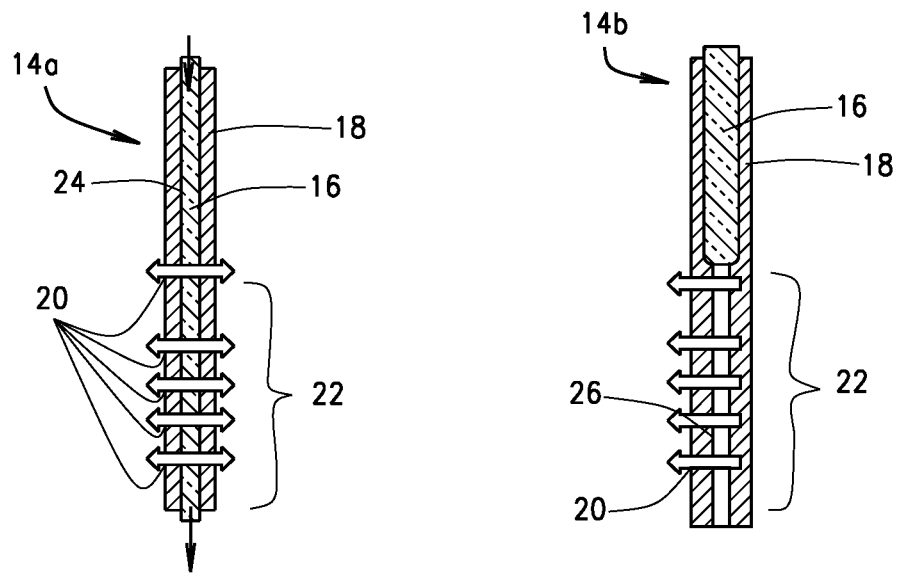
FIG. 2 is a schematic cross-sectional view of a first embodiment of the probe.
FIG. 3 is a schematic cross-sectional view of a second embodiment of the probe.

A first embodiment of the probe 14a of the tip 10 is shown schematically in FIG. 2. The probe 14a includes a core 16 formed from a light transmitting material which is surrounded by a metal sheath 18. The core 16 can, for example, be comprised of a single optical fiber or tube, or a plurality of optical fibers or tubes. The fiber optic core 16 depends from the tip connector 12, and the connector 12 is adapted such that a light source in the driver can deliver light to the fiber optic core 16. The core can be made from Silica fibers (such as glass, $SiO_2$ or fused quartz) and plastic. The fibers can also be made from polymethyl methacrylate or other light conducting polymers, most of which are derivatives of polyacetylene, polyaniline, polypyrrole or polythiophenes.

The metal sheath 18 extends the full length of the core 16. The sheath can comprise a metallic oxide, gold, palladium, chromium, or silver (or a combination thereof). The sheath 18 can be formed as thin metallic coating on the core 16, or it can comprise a tube. If the sheath is in the form of a tube, the probe 14a can be formed, for example, by overcoating the core with the metal sheath material or by coextruding the core 16 and sheath 18. If the sheath 18 is a coating, the sheath can be formed by coating a metal (metallic oxide)

layer on the light conducting core 16 using thin film deposition, sputter coating technology (which can be used with gold, palladium, chromium) or electrophoretic deposition (which can be used with silver). In an alternative, the probe 14a can be formed by 3D printing.

The sheath 18 has a plurality of apertures 20 in a light zone 22 of the probe. This light zone is defined as the portion of the probe which will extend into the root canal. These apertures 20 are dispersed about the surface of the probe 14. The apertures 20 can be formed by a micromachining process (such as, precision drilling) or laser machining. Alternatively, the apertures 20 can be formed by photoresist based pattern technology. If the probe is 3D printed, the apertures 20 can be formed as part of the printing process.

The apertures 20 can define a substantially constant aperture density (i.e., the number or area of apertures/surface area can be substantially constant). Alternatively, the aperture density can vary, with a smaller aperture density in the top portion of the light zone and a higher aperture density in a lower portion of the light zone. Stated differently, the apertures can be formed such that more light exits or enters at the side of the probe in the lower portion of the light zone than in the upper portion of the light zone. Additionally, as seen in FIG. 2, the activator sheath 18 is open at its bottom, such that light can also exit or enter the probe at its bottom.

The metal sheath 18 has a highly reflective inner surface 24 which is adjacent the light transmitting fiber optic core 16. Thus, when light is introduced into the core, the light will be reflected off the inner surface 24 of the sheath 18, and will bounce back and forth across the core, to exit the core when the light reaches an aperture 20 or the bottom opening of the sheath 18. If the core is comprised of a plurality of optical fibers, the length of the fibers can be varied, to provide more control over the level in the probe 14 at which the light exits the side of the activator.

As seen in FIG. 2, the core 16 and the metal sheath 18 are co-extensive (i.e., the bottoms of the core 16 and sheath 18 are at a common plane). However, in FIG. 3, the probe 14b has a sheath 18 extends beyond the bottom of the core 16. In this variation, the light zone 22 of the probe 14b is below the bottom of the core 16, and is hollow. The light zone 22 which is below the core is filled with a liquid 26. The liquid can be water or a liquid which matches the refractive index of the fiber optic core. The refractive index matching liquid can be, for example, chlorofluorocarbon. In the probe 14b, light will exit the core 26 at the bottom of the core and enter the liquid 16. The light will bounce/reflect off the inner reflective surface 24 of the sheath 18 in the light zone 22 until the light either exits through one of the apertures 20 or through the opened bottom of the sheath.

In the probes 14a and 14b (FIGS. 2 and 3), the light zone can have a length of about 16 mm. The portion of the probe above the light zone, which can be termed a connection zone, can have a length of between about 2 mm and about 15 mm, such that the overall length of the probe is between about 18 mm and about 31 mm.

Figure 4:
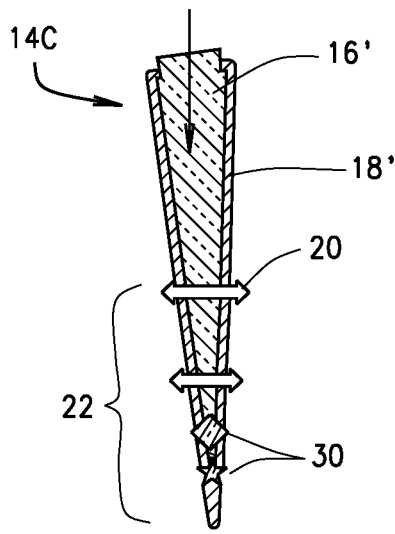
FIG. 4 is a schematic cross-sectional view of a third embodiment of the probe.
Figure 5:
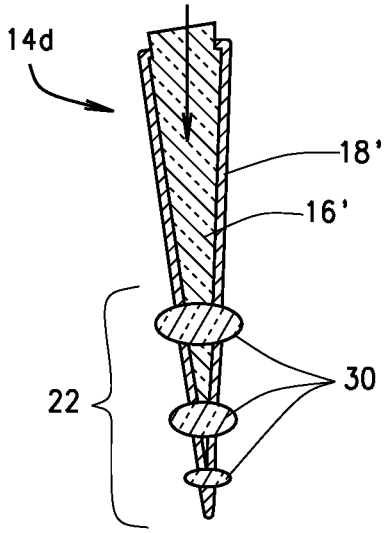
FIG. 5 is a schematic cross-sectional view of a fourth embodiment of the probe.

The probes 14c and 14d of FIGS. 4 and 5 are both tapered. Each can have a taper of about 20% to about 90%, and defines a regular cone (i.e., they form isosceles triangles in vertical cross-section). The probe 14c (FIG. 4), is shown with light diffusers 30 at the bottom of its light zone 22. The probe 14d (FIG. 5) has no apertures. Rather, the probe 14d is provided with a plurality of light diffusers 30. As seen, the sheath 18' for each probe 14c,d extends to the end or apex of the probe, such that the sheath is closed at its bottom. Hence, all light must escape the probe through the apertures or light diffusers in the light zone. The light diffusers can comprise a resin impregnated with light conducting materials (such as polycarbonate or epoxy resin) or light scattering particles (such as diamond dust, TiO2, or alumina). The light diffusers are in contact with the core 16' of the probe 14c,d and protrudes through the sheath 18', thus forming a small protrusion on the outer surface of the sheath 18'.

Figure 6:
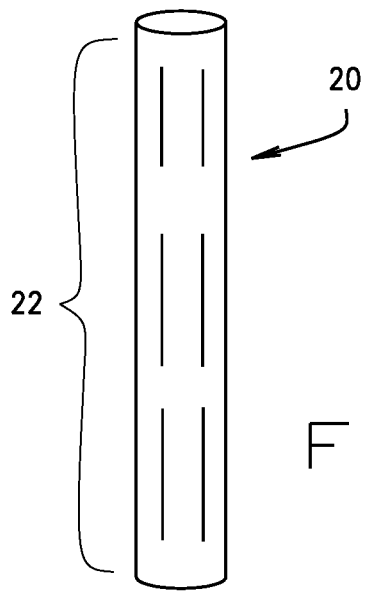
FIG. 6 is an enlarged schematic elevational view of an illustrative light zone of an activator probe.

In the figures, the apertures 20 are shown as holes in the respective sheaths 18, 18'. These holes can be pores which can be formed in the sheath as part of the process of forming the sheath. Alternatively, the holes can be formed subsequently to forming the sheath by means of, for examples, lasers, which will remove the material from the sheath to form the apertures 20. Regardless of how the apertures are formed, the apertures can vary in size, such that some apertures are small apertures and others are large apertures. Hence, small apertures can be formed in the upper portion of the light zone 22 and larger apertures can be formed in the lower portion of the light zone. Further, apertures need not be round. They can be of any desired shape. For example, the apertures can be formed quadrilaterals, triangles, or as slits or slices in the sheath, as shown in FIG. 6. If formed as slits, the aperture density can vary by altering the length of the slits, with shorter slits in the upper portion of the light zone and longer slits in the lower portion of the light zone.

Figures 7, 8:
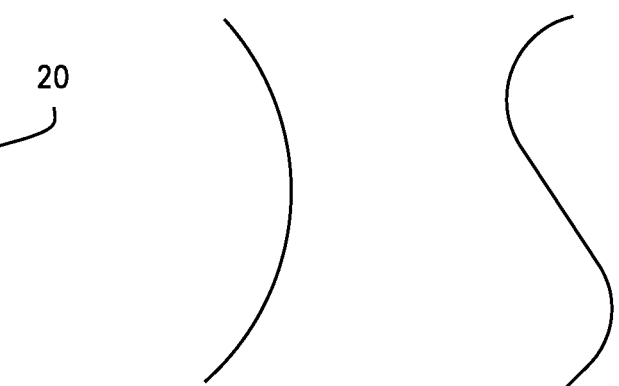
FIGS. 7 and 8 are schematic drawings of generally C-shaped and S-shaped versions of the activator/probe.

The probe is shown in FIGS. 2, 3, and 6 as being generally straight and cylindrical, and in FIGS. 4 and 5 as having a tapered end. However, the probe can have other shapes. For example, the probe can be curved along its length to define a generally C-shaped or S-shaped probe, as seen in FIGS. 7 and 8. If the probe is S-shaped, the probe can be generally planar or the different curves of the probe can be in different planes, such that the probe is "3-dimensional".

Figure 9:
FIG. 9 shows schematic cross-sectional shapes of the activator/probe.

Additionally, the probe need not be generally circular in cross-section, as shown in the drawings. Rather, the probe can be oval or be provided with longitudinal grooves, as shown in FIG. 9. If grooved, the probe can have two, three, four, or more grooves which can be spaced about the probe. These longitudinal grooves can be evenly or unevenly spaced about the perimeter of the probe. Further, for a probe having two or more grooves, the grooves can all be the same size, or the grooves can be of different sizes.

Further, as can be appreciated, the probe is flexible, so that the probe can pass through curvatures in the root canal. If the probe 10 is S-shaped or C-shaped, the shape and flexibility of the probe enables the probe to effectively adapt to the diameter/shape of the canal and to conform, contact, wipe, or otherwise rub against, the surface of the root canal when the probe is activated. Further, the probe can be somewhat springy, such that the probe will contact or push against the walls of the root canal. As can be appreciated, this will facilitate the mechanical disruption of the biofilm layer in the root canal. The probe has a hardness less than the hardness of dentin, and hence, the probe will not cut the dentin or further shape the canal.

Camera

In view of the fact that fiber optics are used, the tip 10 can include at least one fiber optic which sends light up the probe 14 to be captured by a camera chip in the connector 12. As can be appreciated, the light transferred up the probe 14 contains image information (i.e., light reflected from the root canal which then enters the probe in the light zone) of the root canal which is received by the camera chip. The camera chip can then send the information to a receiver, to display the information on a screen, enabling the endodontist to better see the root canal. As is known, currently, endodontists use microscopes to look down the canal during an endodontic procedure. However, using a microscope, the endodontist cannot see past curves in the canal. Further, the instrumentation inserted into the canal can obstruct the endodontist's view of the canal. The use of a camera will provide the endodontist with a better and unobstructed view of the canal.

Delivery of Electrical Field into the Root Canal

It has been determined that electrophoretic currents can be used to deliver charged materials through the root canal anatomy with subsequent deposition of the material in the periapical tissues, lateral canals or dentinal walls. Delivery of the electrophoretic currents requires the use of an intracanal electrode, which will deliver an electric field into the root canal. The tip 10 can be provided with an electrical lead or wire which will connect the metallic sheath 18, 18' of the probe 14a-d to an appropriate power source.

As various changes could be made in the above constructions without departing from the scope of the invention, it is intended that all matter contained in the above description or shown in the accompanying drawings shall be interpreted as illustrative and not in a limiting sense.

The invention claimed is:

1. An endodontic tip for use in endodontic procedures; said tip comprising a probe comprising a core capable of transmitting visible light and a metallic sheath surrounding said core; said sheath defining a reflective inner surface; said probe defining a light zone including a plurality of apertures formed in said sheath such that visible light can exit said light zone of said probe through said apertures; said light zone of said probe being sized and shaped to extend into a root canal; said tip further comprising a connecter adapted to connect the probe to a sonic or ultrasonic driver, said probe being capable of withstanding sonic or ultrasonic vibrations; wherein the apertures in a bottom portion of the light zone are greater in size than the apertures in an upper portion of the light zone such that more light exits the probe in the bottom portion of the light zone than in the upper portion of the light zone.

2. The endodontic tip of claim 1 wherein said apertures are defined by a plurality of perforations and/or slits in said sheath.

3. The endodontic tip of claim 2 wherein said apertures are shaped and configured such that a greater amount of light can exit the side of probe in a bottom portion of the light zone than in an upper portion of the light zone.

4. The endodontic tip of claim 2 wherein said apertures are axially extending elongate apertures.

5. The endodontic tip of claim 1 wherein said core is comprised of a single light transmitting optical fiber or a plurality of light transmitting optical fibers.

6. The endodontic tip of claim 5 wherein the optical fibers of said plurality of optical fibers are of differing lengths.

7. The endodontic tip of claim 5 wherein said endodontic tip further includes a camera, and wherein at least one of said plurality of optical fibers receives light entering said probe through at least one of said apertures and directs light coronally from within the root canal; said camera being configured and adapted to receive light from said at least one optical fiber; said camera being in communication with a receiver, said receiver being adapted to display the image received by said camera.

8. The endodontic tip of claim 1 wherein said metallic sheath is electrically conductive; said tip being adapted to connect said sheath to a source of electricity, such that said tip can induce an electrical field in said root canal.

9. The endodontic tip of claim 1 wherein said sheath is formed by coating said light transmitting core with a desired metal by means of thin film deposition, sputter coating technology, or electrophoretic deposition.

10. The endodontic tip of claim 1 wherein said probe is formed by co-extruding said core and said sheath or by 3D printing.

11. The endodontic tip of claim 1 wherein said sheath is made from a metal oxide, gold, palladium, chromium, silver, and combinations thereof.

12. The endodontic tip of claim 1 wherein said probe is generally straight, generally C-shaped, or generally S-shaped.

13. The endodontic tip of claim 12 wherein said probe is generally planar or 3-dimensional.

14. The endodontic tip of claim 12 wherein said probe is tapered.

15. The endodontic tip of claim 1 wherein said probe, in cross-section, is generally circular or oval.

16. The endodontic tip of claim 1 wherein said probe includes one, two, three, four or more grooves extending longitudinally along an outer surface of said probe.

17. The endodontic tip of claim 16 wherein said grooves are evenly or unevenly spaced about said probe.

18. The endodontic tip of claim 16 wherein said grooves are all the same size or are of different sizes.

19. An endodontic tip for use in endodontic procedures; said tip comprising a probe capable of withstanding sonic or ultrasonic vibrations; said probe comprising a core capable of transmitting visible light and a metallic sheath surrounding said core; said sheath defining a reflective inner surface; said probe defining a light zone including a plurality of apertures formed in said sheath such that visible light can exit said light transmitting zone of said probe through said apertures; said apertures being defined by a plurality of perforations and/or slits in said sheath; said light zone of said probe being sized and shaped to extend into a root canal; said tip further comprising a connecter adapted to connect the probe to a sonic or ultrasonic driver; wherein the apertures in a bottom portion of the light zone are greater in size than the apertures in an upper portion of the light zone such that more light exits the probe in the bottom portion of the light zone than in the upper portion of the light zone.

20. In combination, an endodontic tip for use in endodontic procedures and a sonic or ultrasonic drive;
   said tip being adapted to be connected to said sonic or ultrasonic drive such that, when said sonic or ultrasonic drive is activated, said probe will be sonically or ultrasonically vibrated;
   said tip comprising a probe comprising a core capable of transmitting visible light and a metallic sheath surrounding said core; said sheath defining a reflective inner surface; said probe defining a light zone including a plurality of apertures formed in said sheath such that visible light can exit said light transmitting zone of said probe through said apertures; said light zone of said probe being sized and shaped to extend into a root canal; said tip further comprising a connecter adapted to connect the probe to a sonic or ultrasonic driver.

21. A method of disinfecting a root canal comprising;
   inserting a probe of an endodontic tip into a root canal; the probe comprising a core capable of transmitting visible light and a metallic sheath surrounding said core; said sheath defining a reflective inner surface; said probe defining a light zone including a plurality of apertures formed in said sheath such that visible light can exit said light transmitting zone of said probe through said apertures; said light zone of said probe being sized and shaped to extend into a root canal; said tip further comprising a connecter adapted to connect the probe to a sonic or ultrasonic driver; and transmitting visible light through the probe and inducing sonic or ultrasonic vibrations in the probe.

* * * * *